(12) United States Patent
Lieponis

(10) Patent No.: US 7,857,837 B2
(45) Date of Patent: Dec. 28, 2010

(54) ADJUSTABLE SPINAL SYSTEM

(76) Inventor: Jonas V. Lieponis, 461 Vineyard Point Rd., Guilford, CT (US) 06437

( * ) Notice: Subject to any disclaimer, the term of this patent is extended or adjusted under 35 U.S.C. 154(b) by 531 days.

(21) Appl. No.: 11/757,492

(22) Filed: Jun. 4, 2007

(65) Prior Publication Data

US 2008/0300635 A1 Dec. 4, 2008

(51) Int. Cl.
*A61B 17/58* (2006.01)
*A61B 17/70* (2006.01)
*A61B 17/80* (2006.01)
*A61B 17/88* (2006.01)

(52) U.S. Cl. ............... 606/280; 606/246; 606/279; 606/281; 606/286; 606/290; 606/902; 606/903; 606/901

(58) Field of Classification Search ............... 606/60, 606/246, 279, 280, 281, 286, 290, 902, 903, 606/906
See application file for complete search history.

(56) References Cited

U.S. PATENT DOCUMENTS

2007/0270820 A1* 11/2007 Dickinson et al. ............ 606/61

* cited by examiner

*Primary Examiner*—Thomas C Barrett
*Assistant Examiner*—Sameh Boles
(74) *Attorney, Agent, or Firm*—St. Onge Steward Johnston & Reens LLC

(57) ABSTRACT

A system and method for facilitating the installation of spinals support members on consecutive vertebrae where the optimal positioning of screws does not form a straight line. The system includes a first plate spanning a first and second vertebrae, a second plate spanning the second vertebrae and a third vertebrae and an offset member coupling the first plate to the second plate at a defined angle to accommodate the anatomical variations of the patients vertebrae.

13 Claims, 3 Drawing Sheets

ADJUSTABLE SPINAL SYSTEM

FIELD OF THE INVENTION

The invention relates to a spinal implant and more particularly, to a device for accommodating the particular anatomy of a patient's spine when multiple spinal implants are inserted.

BACKGROUND OF THE INVENTION

Spinal implants have been utilized for a number of years and typically comprise plates or rods affixed to the spine. For any number of reasons, a joint can deteriorate requiring an implant be inserted to various vertebrae.

A common practice has been to provide a pedicle screw in the individual vertebrae and attach a plate spanning the distance therebetween to stabilize the joint and maintain a set distance between the two vertebrae. The goal is to create/maintain normal anatomic relationship of two adjacent vertebrae of the spine. Often the plate is provided with at least one slot allowing for adjustment of the distance between the vertebrae before the implant is secured to the individual pedicle screws. The plate typically comprises a rigid material that will secure the vertebrae it is connected between. This configuration functions fairly well for securing one vertebrae to another.

However, a problem arises when multiple consecutive joints require stabilization. The problem arises due to the various anatomical differences that occur in the spine from patient to patient. For example, optimal pedicle screw spine fixation often requires that pedicle screws inserted into vertebrae are not oriented in a straight line. Therefore, connection of plates from one set of vertebrae to another requires that the plates be offset from one another, either medially or laterally, to maintain normal anatomic angular relationship of two adjacent vertebrae; or that the orientation of the pedicle screws in the vertebrae be adjusted.

The latter approach is disfavored as adjustment of vertebrae to line up the pedicle screws is highly undesirable and may not be possible, as is insertion of the pedicle screws in less optimal locations to achieve a relatively straight line.

Certain systems have been introduced to compensate for various anatomical differences with various levels of success. One such system includes an implantable device that is positioned between two vertebrae, such as for example, a wedge shaped device that is inserted in the location of where the spinal disc would normally reside. However, where removal of the disc is not required or advisable, this type of system is not usable.

In addition, minimal incision implantation is desired compared to open surgery. However, with the present systems, when multiple plates are used to span consecutive vertebrae, typically an incision is made to expose the entire area from vertebrae to vertebrae.

SUMMARY OF THE INVENTION

Accordingly it is desired to provide a system and method for affixing a spinal implant spanning at least two different sets of vertebrae that accounts for the anatomical differences between vertebrae.

It is also desire to provide a system and method for affixing a spinal implant across at least three vertebrae that provides for medial and lateral adjustment of individual plates spanning consecutive spinal joints.

It is further desire to provide a system and method for affixing a spinal implant that permits minimal incision implantation.

It is still further desire to provide a system and method for affixing a spinal implant that permits distraction or compression.

These and other objectives are achieved in one advantageous embodiment, by the provision of at least two plates that may be attached between three pedicle screws to stabilize three consecutive vertebrae relative to each other. Initially, the physician determines the proper location for insertion of the pedicle screws in the three consecutive vertebrae. Once inserted, the surgeon then attaches one of the plates between the first and the second pedicle screws positioning the first and second vertebrae at a desired distance from each other. The physician then determines whether a second plate, which is to be attached between the second and third vertebrae, needs to be attached at an angle (medially or laterally) relative to the first plate. If so, an offset member may be attached between the first and second plates to provide the desired angular offset to accommodate the patient's anatomy.

It is contemplated that the first plate may be provided as an elongated relatively flat plate having an elongated slot provided therein that runs along the longitudinal axis of the plate. In this manner, the plate is slid over the first and second pedicle screws and a threaded cap is installed on the first pedicle screw to firmly affix the plate to the first pedicle screw.

Next, the physician can insert the second plate over the second and third pedicle screws and insert an offset member having two protrusions that engage with the slots of the first and second plates respectively. The offset member serves to maintain the plates at a fixed angle with respect to each other and is selected based upon the patient's anatomy.

Once the first pedicle screw is secured to the plate, the physician can apply either compression or distraction to the second pedicle screw relative to the first pedicle screw to position the first and second vertebrae at a selected distance. Once achieved, a threaded cap is installed on the second pedicle screw to secure the distance between the first and second vertebrae. The physician may then again apply compression or distraction force between the second and third pedicle screws to position the second and third vertebrae at a selected distance. Finally, a threaded cap is installed on the third pedicle screw to secure the distance between the second and third vertebrae. It is contemplated that the offset member may comprise any of a number of angular configurations that may be selected to suit the patient's particular anatomy.

In this manner, multiple plates may be installed on consecutive vertebrae that may not allow for pedicle screws to be installed in a straight line relative to each other.

It is further contemplated that the individual plates may be configured with a cross-bar positioned in the slot forming essentially two consecutive elongated slots in each plate. This provides the advantage of allowing the physician to apply either compression or distraction to the pedicle screws more easily during less invasive surgical procedures. Further, each plate may be provided with a notch at each end, which will also allow for easier application of force on the pedicle screws by the physician.

In one advantageous embodiment an adjustable spinal implant system is provided comprising a first plate having an elongated slot form therein along a longitudinal axis of the first plate and a second plate having an elongated slot form therein along a longitudinal axis of the second plate. The system further comprises an offset member having a opening formed therein to fit over a screw shaft and at least two tabs extending radially outward, the two tabs having centerlines that form an acute angle relative to each other. The system is provided such that the first, second and third screws are insertable in first, second and third vertebrae respectively and the first plate is positioned over the first and second screws and the second plate positioned over the second and third screws. The offset member is positioned over the second screw, the first tab engaged with the slot in the first plate and the second tab engaged with the slot in the second plate.

In another advantageous embodiment a method for installing a spinal implant is provided comprising the steps of installing first, second and third screws to at least three consecutive vertebrae, the first and second screws forming a first plane and the second and third screws forming a second plane that is different from the first plane. The method further comprises the steps of affixing a first plate between the first and second screws, the first plate having a slot located therein and installing an offset member to the second screw, the offset member having a first tab that engages with the slot in the first plate. The method still further comprises the steps of affixing a second plate between the second and third screws, the second plate having a slot located therein and engaging a second tab on the offset member with the slot in the second plate.

Other objects of the invention and its particular features and advantages will become more apparent from consideration of the following drawings and accompanying detailed description.

DETAILED DESCRIPTION OF THE INVENTION

Figure 1:
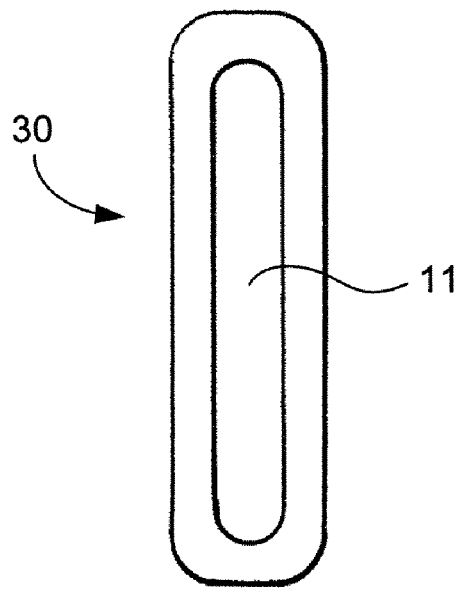
FIG. 1 is an illustration of a plate according to the prior art.

Referring now to the drawings, wherein like reference numerals designate corresponding structure throughout the views.

FIG. 1 illustrates a plate 10 according to the prior art. The plate 10 is generally provided as an elongated device having an elongated slot 11 provided therein for fitting over screws variously positioned in vertebrae.

Figure 2:
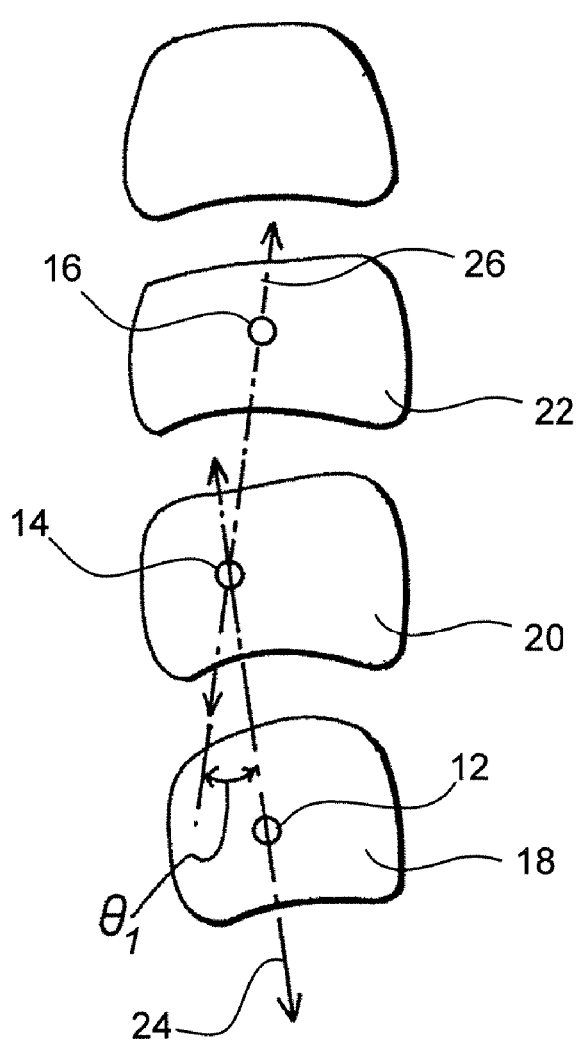
FIG. 2 is an illustration of pedicle screws attached to consecutive vertebrae.
Figure 3:
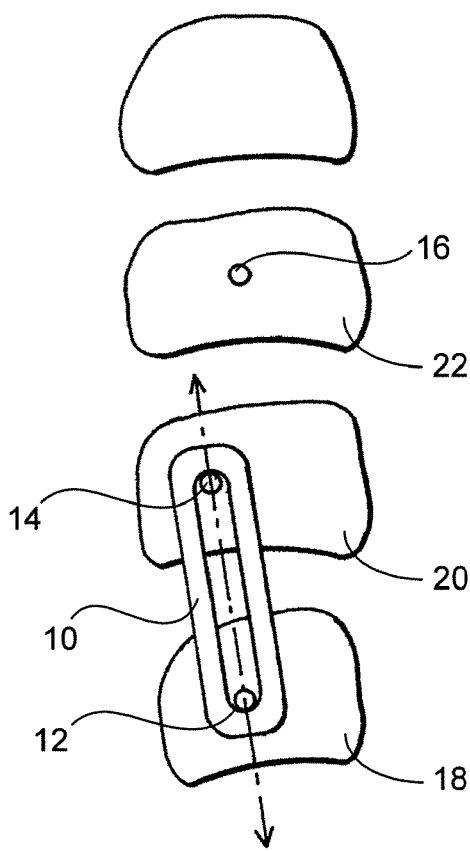
FIG. 3 is an illustration of a plate attached over the pedicle screws according to FIG. 2.

A problem with current systems is illustrated in FIG. 2 where pedicle screws 12, 14, 16 are shown inserted in vertebrae 18, 20, 22 respectively. As seen in FIG. 2, pedicle screws 12, 14 form a first plane 24, while pedicle screws 14, 16 form a second plane 26 that is off set from the first plane 24 by an angle $\theta_1$. However, prior art devices are only capable of being installed in a straight line and can not accommodate medial or lateral offsets, or in this example, angle $\theta_1$. For example, in FIG. 3 first plate 10 is illustrated installed on pedicle screws 12, 14, however, due to the interconnections between prior art plates, a second plate will not be able to be placed between pedicle screws 14, 16 because they do not line up with the pedicle screw 12 along first plane 24. One way to avoid this problem is to install the pedicle screws such that they do actually substantially line up in a relatively straight line. However, often the optimal insertion locations for pedicle screws 12, 14, 16 do not form a straight line.

Figure 5:
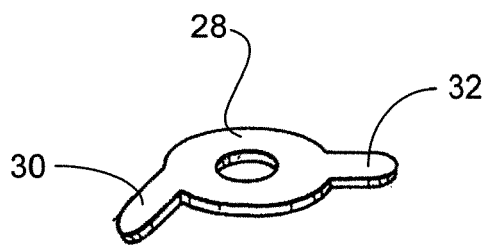
FIG. 5 is a perspective view of the offset member according to FIG. 4.
Figure 4:
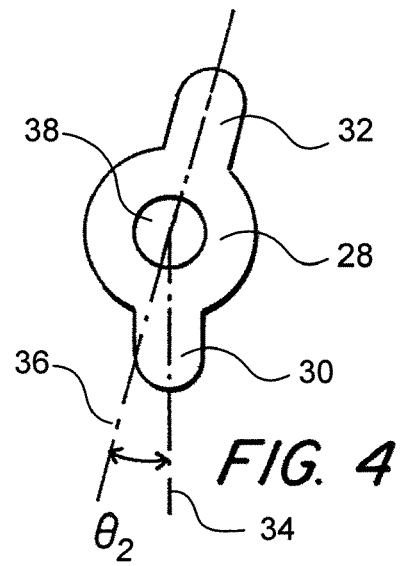
FIG. 4 is an illustration of an offset member for use with the plate according to FIG. 1.

An offset member 28, according to the present invention is provided and illustrated in FIGS. 4 and 5. In this embodiment, offset member 28 is generally provided having a circular perimeter with a first tab 30 and a second tab 32 protruding from the perimeter. As can be seen in FIG. 4, the tabs 30, 32 are off set from each other such that a centerline 34 of first tab 30 is off set from a centerline 36 of second tab 32 by an angle $\theta_2$. It is contemplated that angle $\theta_2$ may comprise virtually any angle such that the physician, upon determining the proper off set angle from first plane 24 and second plane 26, can select the offset member 28 having the proper angle $\theta_2$ to substantially match angle $\theta_1$. It is further contemplated that a number of preset angles, such as for example, but not limited to, the tabs being variously positioned in 1° increments, may be provided.

Offset member 28 is further provided with an opening 38 extending through a center of offset member 28 such that it may be fitted on one of the pedicle screws.

Figure 9:
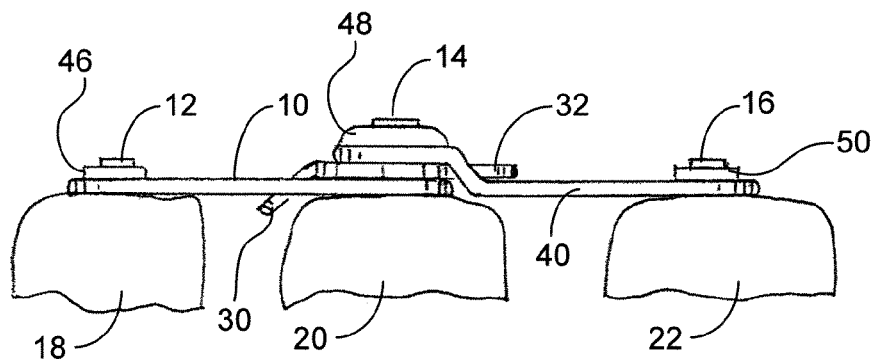
FIG. 9 is perspective view of the first plate, the second plate and the offset member according to FIG. 8.

As can be seen in FIG. 5, in this embodiment, first tab 30 is not only radially off set from second tab 32, but is bent downward relative to offset member 28 and second tab 32 and is more clearly shown in FIG. 9 engaging with elongated slot 11 of plate 10.

Figure 6:
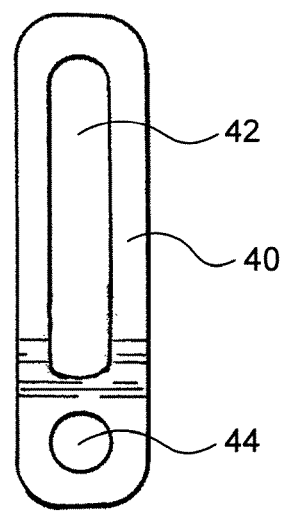
FIG. 6 is an illustration of a second plate to be attached to with the plate shown in FIG. 3.
Figure 7:
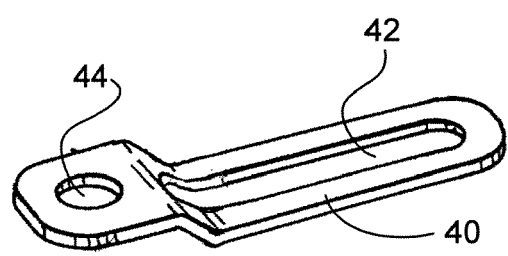
FIG. 7 is perspective view of the offset member according to FIG. 6.

Turning now to FIGS. 6 and 7, second plate 40 is illustrated including an elongated slot 42 and an opening 44. As is more clearly illustrated in FIG. 7, second plate 40 comprises a dog-leg section such that opening 44 reside on a different plane than elongated slot 42.

Figure 8:
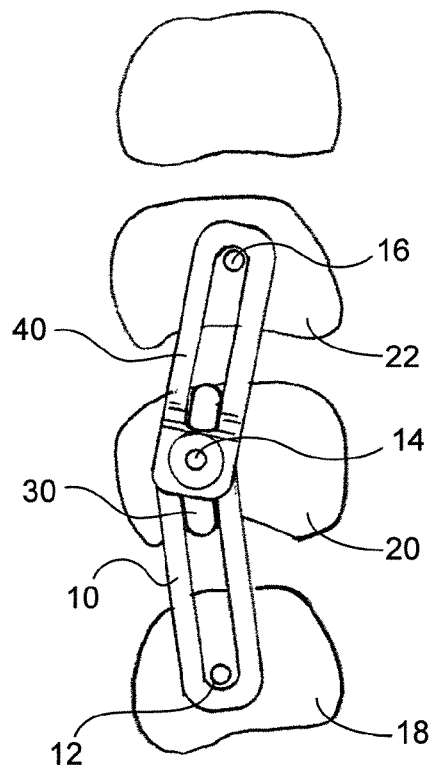
FIG. 8 is an illustration of the first and second plates and the offset member fitted on the pedicle screws according to FIG. 2.

The assembly of first plate 10, offset member 28 and second plate 40 is shown in FIGS. 8 and 9. As illustrated, first plate 10 is inserted over pedicle screws 12, 14, then offset member 28 is inserted over pedicle screw 14, finally second plate 40 is inserted over pedicle screws 14, 16. Based on the angle $\theta_1$, the physician selects the appropriate offset member having angle $\theta_2$ and fits this over pedicle screw 14 such that first tab 30 engages into elongated slot 11. In addition, opening 44 in second plate 40 is fitted over pedicle screw 14 such that second tab 32 engages with elongated slot 42 of second plate 40. In this manner, first plate 10 and second plate 40 are interlocked relative to each other such that rotational movement relative to each other is prevented.

Also shown in FIG. 9 are locking nuts 46, 48, 50, which fit over pedicle screws 12, 14, 16 respectively to firmly lock and secure first and second plates 10, 40 to vertebrae 18, 20, 22.

Figure 10:
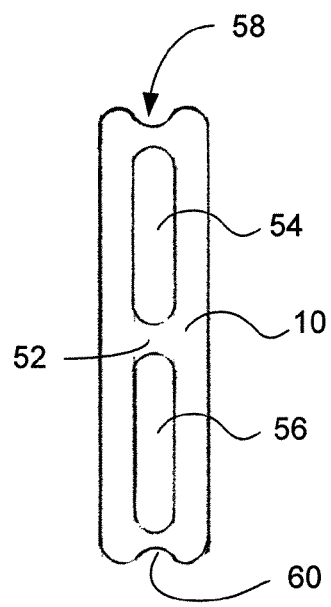
FIG. 10 is an alternative configuration of the plate attached to the pedicle screws illustrated in FIG. 3.

Referring now to FIG. 10, an alternative embodiment for first plate 10 is illustrated having a horizontal bar 52 that forms two elongated slots 54, 56. Also illustrated in FIG. 10 are notches 58, 60 positioned at the ends of plate 10. The notches 58, 60 are formed as grooved portioned that may received a pedicle screw therein such that when a pressure is applied to the screw, the screw will not easily slip off of the end of the plate 10, but rather is maintained within the notch 58, 60.

It is highly desirable to perform a spinal implant procedure with minimal incision to the patient. However, when implanting multiple consecutive plates on vertebrae, this becomes very difficult or impossible for prior art systems. For example, it is desirable to only make an incision over the area where, for example, the pedicle screw is to be affixed to the vertebrae. It should be noted that the plates extend from one vertebra to another. This can be accomplished by fitting the plate under the skin of the patient between the incisions. However, it becomes difficult when using a plate according to the prior art, to provide proper distraction or compression to provide the proper distance between vertebrae. The physician can apply a force to the pedicle screw to either compress or expand the space between vertebrae, however, it is difficult to secure the screw to the plate in the desired position while applying pressure to the screw shaft, especially when performing minimal incision implantation.

The provision of horizontal bar 52 allows the physician to apply distraction or compression to the vertebrae without having to directly apply the pressure to the screw shaft. In addition, the notches 58, 60 also allow the physician to apply distraction or compression to the vertebrae, which may be very difficult to accomplish in minimal incision implantation. However, the physician may insert the plate 10 under the skin spanning the vertebrae with notches 58, 60 used to capture a screw shaft such that a pressure may be applied thereto to set a distance between vertebrae. In any event, the horizontal bar 52 and notches 58, 60 provide additional surfaces for the physician to apply pressure to in manipulation of the vertebrae.

While horizontal bar 52 and notches 58, 60 are illustrated on first plate 10, it is contemplated that second plate 40 may also be provided with a horizontal bar positioned within elongated slot 42 notches positioned at either end of second plate 40.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An adjustable spinal implant system comprising:
   a first plate having an elongated slot form therein along a longitudinal axis of said first plate;
   a second plate having an elongated slot form therein along a longitudinal axis of said second plate;
   an offset member having a opening formed therein to fit over a screw shaft and at least two tabs extending radially outward, the two tabs having centerlines that form an acute angle relative to each other; and
   first, second and third screws insertable in first, second and third vertebrae respectively;
   said first plate positioned over said first and second screws and said second plate positioned over said second and third screws;
   said offset member positioned over said second screw, said first tab engaged with the slot in said first plate and said second tab engaged with the slot in said second plate;
   wherein said offset member is positioned between said first and second plates and said second plate is provided with an offset such that said second plate may be positioned on said second screw over said first plate and said offset member; and
   wherein said second tab extends substantially in the same plane as the offset member to engage with said slot in said second plate, and said first tab extends in a plane different from said offset member to engage with said slot in said first plate.

2. The adjustable spinal implant system according to claim 1 further comprising first, second and third locking nuts fitted over said first, second and third screws respectively.

3. The adjustable spinal implant system according to claim 1 wherein said first plate comprises a horizontal bar segmenting the slot in the first plate into first and second elongated slots.

4. The adjustable spinal implant system according to claim 1 wherein said first plate comprises first and second ends and includes a notch positioned in at least one of said first or second ends.

5. The adjustable spinal implant system according to claim 4 wherein said first plate includes a notch positioned in both the first and second ends.

6. The adjustable spinal implant system according to claim 1 wherein said first, second and third screws comprise pedicle screws.

7. The adjustable spinal implant system according to claim 1 wherein said first plate further includes a bar extending laterally across said elongated slot to form two elongated slots.

8. A method for providing a spinal implant system comprising the steps of: forming a first plate having an elongated slot provided therein along a longitudinal axis of said first plate; forming a second plate having an elongated slot provided therein along a longitudinal axis of said second plate; forming an offset member having a opening provided therein to fit over a screw shaft and at least two tabs extending radially outward, the two tabs having centerlines that form an acute angle relative to each other; and providing first, second and third screws insertable in first, second and third vertebrae respectively; wherein the first plate formed to be positioned over the first and second screws and the second plate is formed to be positioned over the second and third screws; and wherein the offset member is formed to be positioned over the second screw between said first and second plates
   and said second plate is provided with an offset such that said second plate may be positioned on said second screw over said first plate and said offset member; the first tab is provided to be engaged with the slot in the first plate and the second tab is provided to be engaged with the slot in the second plate, wherein said second tab extends substantially in the same plane as the offset member to engage with said slot in said second plate, and said first tab extends in a plane different from said offset member to engage with said slot in said first plate.

9. The method according to claim 8 further comprising the step of providing first, second and third locking nuts to be fitted over the first, second and third screws respectively.

10. The method according to claim 8 wherein the first plate includes a horizontal bar segmenting the slot in the first plate into first and second elongated slots.

11. The method according to claim 8 wherein the first plate includes first and second ends and further includes a notch positioned in at least one of the first or second ends.

12. The method according to claim 11 wherein the first plate includes a notch positioned in both the first and second ends.

13. The method according to claim 8 further comprising the step of forming a bar extending laterally across the elongated slot of the first plate to form two elongated slots.

* * * * *